US00RE34075E

United States Patent [19]

Purcell et al.

[11] E Patent Number: Re. 34,075

[45] Reissued Date of Patent: Sep. 22, 1992

[54] DERMAL USES OF TRANS-RETINOIDS FOR THE TREATMENT OF CANCER

[75] Inventors: William P. Purcell; Harlie A. Parish, Jr., both of Memphis, Tenn.

[73] Assignee: Molecular Design International, Inc., Memphis, Tenn.

[21] Appl. No.: 732,091

[22] Filed: Jul. 18, 1991

Related U.S. Patent Documents

Reissue of:

[64] Patent No.: 4,994,491
Issued: Feb. 19, 1991
Appl. No.: 284,185
Filed: Dec. 14, 1988

U.S. Applications:

[63] Continuation-in-part of Ser. No. 67,536, Jun. 29, 1987, Pat. No. 4,885,311.

[51] Int. Cl.[5] ..... A61K 31/38; A61K 31/40; A61K 31/44; A61K 31/215

[52] U.S. Cl. ..... 514/529; 514/354; 514/355; 514/423; 514/425; 514/448; 514/461; 514/512; 514/522; 514/547; 514/548; 514/549

[58] Field of Search ..... 514/529, 354, 355, 423, 514/425, 448, 461, 512, 522, 547, 548, 549

[56] References Cited

U.S. PATENT DOCUMENTS 4,877,805 10/1989 Kligman ..... 514/381

*Primary Examiner*—Allen J. Robinson
*Attorney, Agent, or Firm*—Waldron & Associates

[57] ABSTRACT

The dermal use of non-irritating retinoids such as the esters and amides of 13-cis and 13-trans-retinoic acid for effecting the reduction and reversal of photoaging and skin cancer is disclosed.

5 Claims, No Drawings

DERMAL USES OF TRANS-RETINOIDS FOR THE TREATMENT OF CANCER

Matter enclosed in heavy brackets [ ] appears in the original patent but forms no part of this reissue specification; matter printed in italics indicates the additions made by reissue.

*CROSS-REFERENCE TO RELATED APPLICATION*

*This application is a Continuation-in-Part of application Ser. No. 67,536, filed Jun. 29, 1987 (now U.S. Pat. No. 4,885,311, issued Dec. 5, 1989).*

BACKGROUND OF THE INVENTION

1. Field of the Invention

This invention relates to dermal uses of non-irritating retinoids and particularly to dermal uses of the esters and amides of certain stereoisomers of retinoic acid.

2. Description of the Prior Art

Chronic sun exposure has been determined to create a number of skin disorders including skin cancer which is usually discernible by the presence of lesions known as keratoses as well as photoaging (or "dermatoheliosis") of the skin which is characterized by wrinkling, sallowness, roughness and mottled pigmentation. In a recent article entitled, "Topical Tretinoin Improves Photoaged Skin," JAMA 259, vol. 4, pgs. 527–532, Jan. 22/29, 1988, the authors Webb et al. report that photoaging of the skin of middle-aged and elderly Caucasians could be improved within a 16-week period by daily topical application of a cream containing 0.1% tretinoin (all-trans-retinoic acid).

A side effect reported in the article which complicates the administration of tretinoin, is that the therapy is irritating to the skin and induces dermatitis of several weeks duration in almost all of the subjects undergoing the tretinoin therapy. Redness, peeling, stinging, burning and dryness were consistently experienced by nearly all subjects. Eleven of fifteen subjects experienced dermatitis severe enough to require the use of topical steroids to control the dermatitis. Three of fifteen withdrew from the tretinoin therapy due to the severity of the tretinoin-induced dermatitis. Also positive effects on the histology of the epidermal and stratum corneum layers of the dorsal forearm skin were noted in the tretinoin treated areas. Because of these side effects, recommendation for use of the therapy is inhibited and is not used to full advantage. A method of dermal therapy that would retain the effectiveness of tretinoin but which would be essentially non-irritating would provide a much needed solution to the treatment of photoaging. Further, non-irritating effective treatment of other skin disorder such as skin cancer would meet a long felt need in dermal therapy.

SUMMARY OF THE INVENTION

The present invention is directed to a method for retarding and reversing the effects of skin cancer and photoaging without the inducement of dermatitis wherein there is applied topically to the peidermis of the skin a non-irritating retinoid comprised of the esters and amides of the 13-cis and 13-trans-stereoisomers of retinoic acid, the retinoids having the formulae:

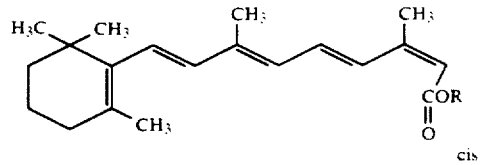

cis

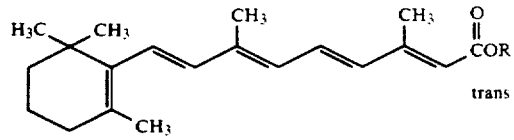

trans wherein R is

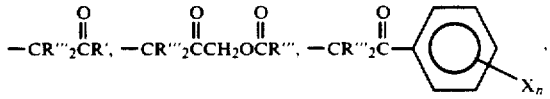

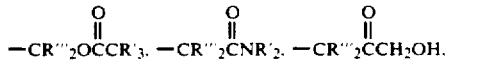

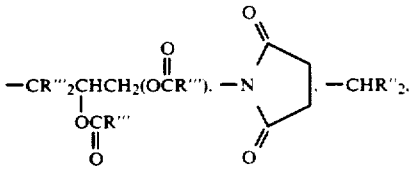

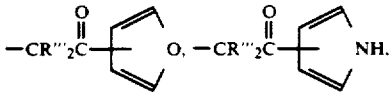

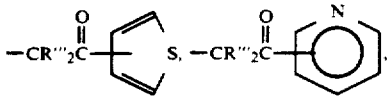

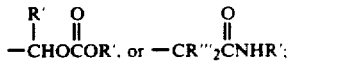

wherein X is

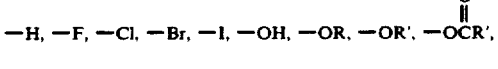

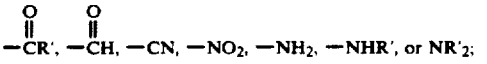

wherein n is a number from 1 to 5; wherein R′ is H or any of the lower alklys ranging from $C_1$ to $C_6$; wherein each R‴ is R′ or the hydrocarbon backbone of fatty acids; and further, where there are two or more R′; R″, or R‴ groups attached to the same carbon or nitrogen, each R′, R″, or R‴ group may be the same as or different from the other, R′, R″, or R‴ groups attached to that carbon or nitrogen.

The esters and amides of 13-cis-retinoic acid and 13-trans-retinoic acid are known to the art. For example, U.S. Pat. No. 4,677,120, the teachings of which are incorporated herein by reference, discloses the use of esters and amides of 13-cis-retinoic acid for the treatment of acne. Illustrative compounds include 1-(13-cis-retinoyloxy)-2-propanone,
1-(13-cis-retinoyloxy)-3-decanoyloxy-2-propanone,
1,3-bis-(13-cis-retinoyloxy)-2-propanone,
2-(13-cis-retinoyloxy)-acetophenone,
13-cis-retinoyloxy methyl 2,2-dimethyl propanoate,
2-(13-cis-retinoyloxy)-n-methyl-acetamide,
1-(13-cis-retinoyloxy)-3-hydroxy-2-propanone, —1-(13-cis-retinoyloxy)-2,3-dioleoylpropanone, —and succinimdyl 13-cis-retinoate.

The esters and amides of 13-trans-retinoic acid are disclosed in copending patent application U.S. Ser. No. 067,536 filed Jun. 29, 1987, now U.S. Pat. No. 4,885,311 and assigned to the assignee of the present application, the teachings of which are also incorporated herein by reference. Illustrative compounds include 1-(all-trans-retinoyloxy)-2-propanone and
2-(all-trans-retinoyloxy)-4'-methoxyacetophenone.

Although the esters and amides of 13-cis-retinoic acid and 13-trans-retinoic acid are known to the art for the treatment of acne and similar dermatological disorders, the utility of these retinoid compounds for the non-irritating treatment of skin cancer and photoaging has not been observed previously.

In addition to the use of the esters and amides of the 13-bis or trans stereoisomer of retinoic acid for the retardation and reversal of photoaging, the use of these compounds extends to non-irritating treatments involving the retardation and reversal of additional dermatological and cosmetic conditions which are ameliorated by tretinoin such as the effacement of wrinkles, improvement in appearance, namely color and condition of the skin, spots caused from exposure to the sun as well as other skin disorders such as the decrease or elimination of skin cancers.

For the treatment of conditions such as are enumerated above, therapeutic retinoid compositions of this invention in the form of lotions or creams are preferable. Such creams or lotions are applied thinly to the involved areas of the skin in frequencies of once to twice daily, the frequency selected being that which is most suitable to the user.

Thus in practicing the treatment of skin disorders such as skin cancer and photoaging in accordance with the practice of the present invention, the esters and amides of 13-cis or trans retinoic acid are topically applied to the skin site exhibiting skin cancer or photoaging in any suitable pharmaceutically-acceptable vehicle, as for example, a liquid carrier such as propylene glycol-ethanol. A preferred liquid composition is a solution of a small amount of at least one of the compounds of the invention in a combination of (A) from about 25% to about 75% by volume of 95% ethanol and (B) from about 75% to 25% by volume of a liquid glycol. A small but effective amount of an antioxidant such as butylated hydroxytoluene may also be included in the composition. A typical solvent carrier of this type comprises 70% by volume 95% ethyl alcohol and 30% by volume propylene glycol. An antioxidant at a concentration of 0.01 to about 0.1% by weight may be incorporated in the carrier. The preferred concentration of the active compound in these compositions is at least about 0.01% by weight, more preferably from about 0.01% to about 0.5% by weight and most preferably from about 0.05% to about 0.2% by weight, but any therapeutically effective concentration may be used. This method of use is similar to the method taught in U.S. Pat. No. 4,677,120 of Parish, et al., the teachings of which are incorporated herein by reference.

The practice of the present invention is illustrated by the following examples:

EXAMPLE I

Topical Assay

The usefulness of the retinoid compounds of the present invention for the inhibition of skin cancers was demonstrated by testing in the ornithine decarboxylase (ODC) assay an ester of tretinoin represented by the formula

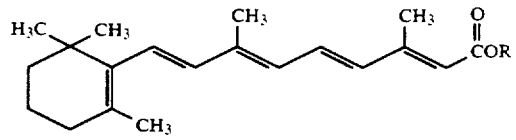

wherein R is —$CH_2COCH_3$ (Compound I, 1-(all-trans-retinoyloxy)-2-propanone) and an ester of isotretinoin represented by the formula

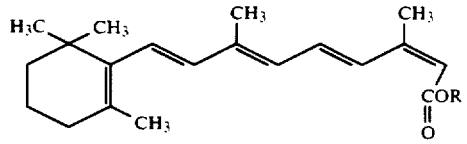

wherein R is

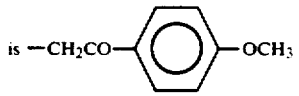

(Compound II, 2-(13-cis-retinoyloxy)-4'-methoxyacetophenone).

The ODC/Retinoid Bioassay is based on the method of Verma, A. K. and Boutwell, R. K., Cancer Res. (1977) 37:2196–2201. The ODC assay measures a compound's effect on the prevention of the induction of ODC, namely the effect of the retinoid compound on the inhibition of the tumor promoter 12-O-tetradecanoylphorbol-13-acetate (TPA) induced ODC activity. The assay was carried out using CD-1 mice (aged 7 to 9 weeks). The dorsal hair of the mice was shaved 3–4 days before testing. Four mice were used for each point. The test retinoids, at one of two dose levels (1.7 and 17 nmoles) dissolved in 0.2 ml of acetone was applied topically to the back of each shaved mouse. A single dose of TPA (17 nM) was applied to the back of each treated mouse 30 minutes later. Control groups were treated with either acetone alone, TPA, or tretinoin. The mice were killed by cervical dislocation 5 hours after TPA treatment.

The dorsal skin encompassing the shaved and TPA exposed area was excised and placed in a 100 ml beaker containing distilled water maintained at 51°–57° C. The skin was soaked for 50–70 seconds at this temperature with intermittent stirring. The skin was placed epidermis side up in a chilled (0°–5° C.) stainless steel plate and the epidermal layer was scraped off with a razor blade. The epidermal layers from the 4 mice were pooled and placed in a homogenization tube with 2 ml of ODA buffer (10 nM tris-HCl with 0.050 nM pyridoxal phosphate, 0.050 nM ethylenediaminetetraacetic acid (EDTA), 1 mM dithiothreitol, pH 7.5). The pooled epidermal layers were homogenized for 15 seconds at 0° C. using a Polytron homogenizer at a setting of 7.5. The homogenate was centrifuged at 30,000×g and the supernatant fraction was pipetted into a storage tube and frozen for about 72 hours.

The homogenate was assayed for ODC activity as described by Verma and Boutwell to measure the release of 14C—$CO_2$ from labelled DL(1-14C) ornithine. Incubations were carried out in disposable centrifuge tubes with center well holders containing filter paper impregnated with sodium hydroxide to absorb 14C—$CO_2$. The incubation mixture consisted of 90 μl of L-ornithine, 350 μl of ODC buffer, 100 μl of 14C-ornithine (1.32 nm, Sp. Act:4.4 pCi/pM) and 10 μl of test sample. After incubation at 37° C. for 45 minutes, 0.5 ml of 2M chilled citric acid (4° C.) was added and incubation was continued for an additional 30 minutes to insure complete absorption of 14C—$CO_2$. The filter paper was removed from the center well holders and set in 1 ml of water in capped scintillation vials for at least 1 hour before adding RBI 3820 scintillation cocktail. Radioactivity was measured in a Tri Carb Scintillation Counter. Results were expressed as pmol of 14C—$CO_2$ released in 30 minutes per milligram of protein based on the specific activity of DL-14C-ornithine. The results are expressed in the Table below as the % reduction in ODC activity as compared to the control.

TABLE

| Compound | Concentration (nM) | ODC Activity (nM $CO_2$/30 min/mg Protein) % Reduction |
|---|---|---|
| I | 17 | 76 |
| | 1.7 | 74 |
| II | 17 | 59 |
| | 1.7 | 0 |
| Acetone | 0.0 | NA* |
| TPA | 17 | 0 |
| Tretinoin | 17 | 87 |

*NA = not available

The results recorded in the Table indicate that the retinoid compounds of the present invention possess biological activity that inhibits TPA induced ODC activity rendering these compounds useful for treating malignant skin disorders.

EXAMPLE II

Compound II of Example I (2-(13-cis-retinoyloxy)-4'-methoxy-acetophenone) was evaluated for its potential to produce primary dermal irritation after a single topical application to the skin tissue of rabbits.

Twelve healthy, young, adult, female New Zealand White rabbits (Orycetolagus cuniculus), were used in the study. The animals were purchased from a registered commercial breeding laboratory. At the start of the study, the animals were in the weight range between 2.0 and 3.0 kilograms, and were approximately 11 weeks of age. Animals selected for the test were not subjected to any previous experimental procedures, and their skin was free from irritation, trauma and disease.

A dose of 0.5 ml of a test solution composed of 0.025 g of 2-(13-cis-retinoyloxy)-4'-methoxyacetophenone in a liquid solution composed of 75 ml of ethyl alcohol, 25 ml of propylene glycol 400, and 0.025 g by weight of butylated hydroxytoluene was applied to one intact and one abraded skin site per animal. Six animals were treated in this manner.

A control group of six animals was treated in an identical manner except that 2-(13-cis-retinoyloxy)-4'-methoxyacetophenone was absent from the control solution.

The application sites were prepared by clipping the skin of the trunk free of hair approximately 24 hours before application of the dose. One application site on each animal was abraded by making minor incisions through the stratum corneum, but not sufficient to disturb the derma (that is, not sufficiently deep to produce bleeding). The second application site was intact skin.

The dose was applied to a small area (approximately 6 $cm^2$) of skin and covered with a gauze patch which was held in place with Vetrap bandaging. The patches were applied to one intact site and one abraded site per animal. The test substance was kept in contact with the skin for 24 hours. The skin was not rinsed following the 24 hour exposure period.

Animals were observed for signs of erythma and edema 24 and 72 hours after application of the test material. Observations were scored according to the "Draize Scale for Scoring Skin Reactions" as in Draize, J. H., "Dermal Toxicity", Appraisal of the Safety of Chemicals in Foods, Drugs and Cosmetics Dermal Toxicity, pp. 46–59, Association of Food and Drug Officials of the U.S., Topeka, Kans., 1965. Observations at the different scheduled times indicated that no signs of erythema or edema formation were evident in any of the 12 test animals at any observation time period. Animals were weighed at the beginning and at the end of the observation period. All 12 animals exhibited a gain in body weight. No overt signs of toxicity were evident during the course of the study.

EXAMPLE III 2-(13-cis-retinoyloxy)-4'-methoxyacetophenone was evaluated in a study of its potential to produce dermal irritation. Comparisons were made of tretinoin, isotretinoin, 2-(13-cis-retinoyloxy)-4'-methoxyacetophenone, and the vehicle solution.

In the first test, four solutions were used. The control consisted of vehicle solution, namely a solution of 60% by volume ethanol and 40% by volume polyethylene glycol. The other three solutions were 0.025% solutions of tretinoin, isotretinoin, or 2-(13-cis-retinoyloxy)-4'-methoxyacetophenone in 60% by volume ethanol and 40% by volume polyethylene glycol. Four patients painted two saturated Q-tips-full of each of the four solutions on four different areas of the inner forearm, twice daily for ten days. No irritant reactions occurred.

In the second test, four other solutions were used. The control consisted of vehicle solution, namely a solution of 90% by volume ethanol and 10% by volume polyethylene glycol. The other three solutions were 0.075% solutions of tretinoin, isotretinoin, or 2-(13-cis-retinoyloxy)-4'-methoxyacetophenone in 90% by volume ethanol and 10% by volume polyethylene glycol. Four patients painted two saturated Q-tips-full of each of the four solutions on four different areas of the inner forearm, twice daily for ten days. Only one subject experienced an irritant reaction. On day two, the tretinoin area began reacting with redness and peeling. On day seven, the isotretinoin area began reacting with redness and peeling. By day nine, both areas were still reacting—the tretinoin area more intensely than the isotretinoin area. There was no reaction in either the 2-(13-cis-retinoyloxy)-4'-methoxyacetophenone or the control areas.

In the third test, three solutions were used. The three solutions were 0.075% solutions of tretinoin, isotretinoin, or 2-(13-cis-retinoyloxy)-4'-methoxyacetophenone in 90% by volume ethanol and 10% by volume polyethylene glycol. Four patients painted two saturated Q-tips-full of the 2-(13-cis-retinoyloxy)-4'-methoxyacetophenone solution twice daily on one cheek of their faces. To the other cheek they applied two saturated Q-tips-full of either tretinoin or isotretinoin.

The tests were carried out in double-blind fashion, that is, neither the subjects nor the investigator knew the contents of the solutions during the study.

Clinical assessments were made daily of the subjects' cheeks. All subjects developed irritant reactions by the third or fourth day of the study. Cheeks of subjects painted with solutions containing 2-(13-cis-retinoyloxy)-4'-methoxy-acetophenone were found to be slightly irritated or not irritated at all during the six days the study was conducted. By way of contrast, the cheeks of subjects painted with solutions containing tretinoin or isotretinoin developed reactions which were so intense with redness and peeling that all subjects discontinued application on or before the sixth day of the study.

EXAMPLE IV

Four subjects aged 49 to 73, three females and one male having significant, easily observed, sun-damaged, wrinkled, "aged" skin of the face and forearms were subjects of a study to determine the effect of topical application of 2-(13-cis-retinoyloxy)-4'-methoxyacetophenone in the treatment of dermatoheliosis. The three females had moderately severe sun-damaged skin and wrinkles of the forearms, hands and face. The one male (aged 73) had extremely severe sun damage in these areas as well as multiple actinic keratoses. The four subjects were provided with and applied to their entire faces (omitting the eyelids) and dorsal surface of the right forearm, once daily for 12 to 16 weeks, 0.1% concentration of 2-(13-cis-retinoyloxy)-4'-methoxyacetophenone in a hydrophilic cream vehicle. The left forearm of each patient was treated daily with a non-medicated moisturizer of the patients' choice.

All subjects were evaluated every 4 weeks through the study for redness, peeling, skin surface texture and wrinkling. Biopsies (using a 4 mm punch) were taken from the dorsal surface of the right upper forearm at the beginning of the study and again from the same area at the end of the study. The biopsies were stained with H & E, Alcian Blue and collagen/elastic stains and compared by a qualified dematopathologist.

Facial assessment of the patients indicated that all showed an improvement in their dermatoheliosis. Two of the four patients showed very significant improvement in facial smoothness, dryness and fine wrinkling. Moderate improvement of these parameters were observed in the other two patients. The improvements began at about two months into the study and continued throughout the remainder of the study.

All the patients involved in the study were pleased by the improved appearance of their skin and noted that they felt their facial skin was fresher, clear and prettier during the study.

Assessment of the forearms of the patients indicated that three showed improvement in surface texture (smoothness), surface dryness and fine wrinkling within two months after application of the cream containing 2-(13-cis-retinoyloxy)-4'-methoxy-acetophenone had been initiated. This improvement was maintained throughout the remainder of the study and was readily apparent when right and left forearms were compared. The one patient who did not show improvement had only used sparing application of the cream containing 2-(13-cis-retinoyloxy)-4'-methoxyacetophenone and had limited treatment to one small spot on the forearm.

No significant irritation was experienced by any patient. Very slight pinkness and a feeling of slight tightness in facial skin developed in two patients after more liberal use of the cream was encouraged.

Comparison of the biopsies taken at the onset of the study with those taken after the treatment period indicated no significant differences in before treatment and after treatment biopsies.

While this test did not have a control, the results were compared with the results obtained from a similar study conducted by Weiss et al. in which 0.1% concentration of retinoic acid in a hydrophilic cream vehicle or vehicle alone was applied to facial skin and dorsal forearm skin. In the Weiss study, it was observed that vehicle alone had no clinical or histological effect but that retinoic acid cream, after 16 weeks of use had some positive effects on the surface texture and wrinkling of sundamaged facial skin, and on the histology of the epidermal and stratum corneum layers of dorsal forearm skin. Also noted in this study was a moderately severe irritancy level from using retinoic acid cream.

EXAMPLE V

The preparation of the compounds of the present invention is illustrated by the preparation of compounds I and II of Example I.

SYNTHESIS OF COMPOUND I 1-(all-trans-retinoyloxy)-2-propanone

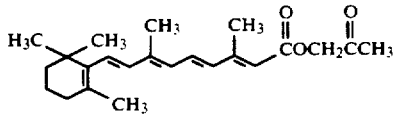

Into a 100 ml round bottom flask was added 1.0 g (0.0033 moles) of tretinoin (retinoic acid from Sigma Chemical Co., St. Louis, Mo.), 25 ml of anhydrous methanol, and 0.2 g (0.0035 moles) of KOH. The solution was stirred at room temperature until the tretinoin dissolved. After the solvent was removed under vacuum, 25 ml of acetonitrile was added and the solution was again concentrated to a semisolid under vacuum. Chloroacetone, (2.0 g, 0.032 moles), 0.1 g 18-crown-6 (0.00038 mole), and 100 ml of acetonitrile were added. The solution was stirred for 24 hours at room temperature with a magnetic stirrer. The sample was concentrated to about 5 ml and chromatographed on a neutral aluminum oxide (Aldrich #19,997-4) column (14×1.8 cm). The alumina was deactivated with 20 ml of water per 1.0 kg of alumina.

The sample was eluted stepwise with 100 ml of 20% dichloromethane in hexane, 100 ml of 50% dichloromethane in hexane, and finally with 250 ml of dichloromethane. The sample eluted quickly and the vast majority of the impurities remained on the column. Fractions of 25 ml were collected and evaluated by thin layer chromatography (TLC) on silica gel (EM Reagents

#5775) developed with ethyl acetate:heptane (1:3). The fractions containing the product were combined and concentrated to give an orange oil which solidified on cooling to give 0.55 g of solid.

Triturating the sample with 10 ml of cold 95% ethanol raised the melting point to 93°-94° C.

TLC on silica gel (EM Reagents #5735) developed with 1:3 ethyl acetate:heptane showed one spot, $R_f$=0.41. TLC on aluminum oxide (EM Reagents #5581) developed with 1:3 ethyl acetate:heptane showed one spot, $R_f$=0.73.

The NMR ($CDCl_3$) spectrum of Compound I taken with a Varian EM 360-A spectrometer was identical to the spectrum of tretinoin except for two additional peaks and the lack of a carboxylic acid peak. The two additional peaks were at 4.5 ppm (singlet, 2 protons, —$OCH_2CO$—) and 2.1 ppm (singlet, 3 protons —$COCH_3$).

Elemental analysis for the compound gives a theoretical value for $C_{23}H_{32}O_3$ of 77.49% C and 0.05% H; the found values were 77.52% C and 9.17% H.

SYNTHESIS OF COMPOUND II 2-(13-cis-retinoyloxy)-4'methoxyacetophenone

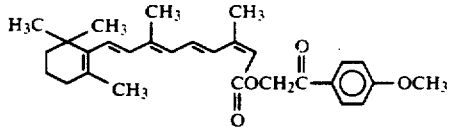

To a 100 ml round bottom flask was added 2.0 g (0.0066 moles) 13-cis-retinoic acid, 1.37 g (0.0042 moles) cesium carbonate, 1.49 g (0.010 moles) 2-chloro-4'-methoxyacetophenone (a lachrymator), and 15 ml of dry dimethylformamide. The reaction mixture was stirred for 18 hours.

After this time, the reaction mixture was poured into 100 ml of water. The solution was stirred for a few minutes and the product separated as a semisolid which was collected by filtration. The product was crystallized from ethanol to give 2.3 g (78% yield) mp 126°-129° C. TLC showed minor impurities. The sample was recrystallized from 80 ml of 95% ethanol and allowed to cool to give 1.6 g (54% yield) mp 132°-134° C.

TLC on Silica gel (EM Reagents #5735) developed with ⅓ ethyl acetate/heptane showed one spot, but the $R_f$ of Compound II was identical to the $R_f$ 2-chloro-4'-methoxyacetophenone which is 0.77. The two can be separated on aluminum oxide (EM Reagents #5581) developed with ½ ethylacetate/heptane. The $R_f$ of Compound II was 0.69. The $R_f$ of the chloro compound is 0.63.

The NMR (CDC13) of Compound II was identical to the spectrum of isotretinoin except for three additional peaks and the lack of a carboxylic acid peak. The additional peaks were at 3.72 ppm (singlet, 3 protons, —$OCH_3$), 5.15 ppm (singlet, 2 protons, —$OCH_2CO$—), and 6.60, 6.75, 7.55 and 7.70 (quadruplet, 4 protons, aromatic ring). Elemental analysis for the compound gave a theoretical value for $C_{29}H_{36}O_4$ of % C 77.64, % H 8.90; the found values were % C 77.71, % H 8.14.

I claim:

1. A method for retarding and reversing the effects of skin cancer in a human subject requiring said treatment without the inducement of dermatitis which comprises topical application on a cancerous dermal site of said human subject a pharmaceutical composition which comprises an effective skin cancer treatment amount of a non-irritating retinoid having the formula

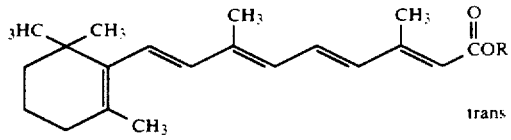

wherein R is a member of the group consisting of

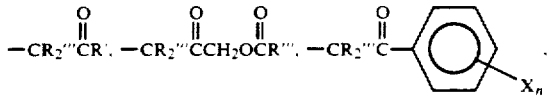

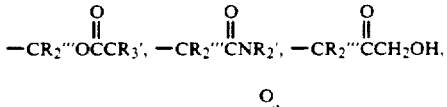

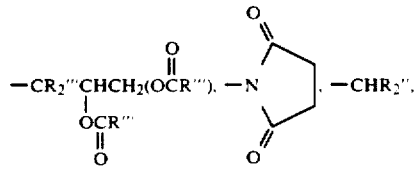

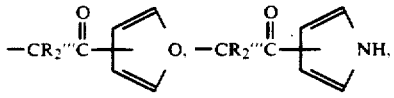

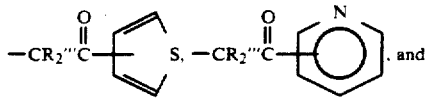

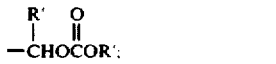

wherein X is a member of the group consisting of

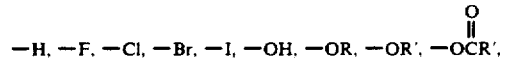

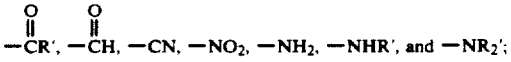

wherein n is a number from 1 to 5;

wherein R' is a member of the group consisting of H and any of the lower alkyls ranging from $C_1$ to $C_6$; wherein R'' is a member of the group consisting of

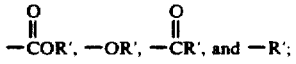

wherein each R''' is a member of the group consisting of R' and the hydrocarbon backbone of fatty acids; and further, where there are two or more R', R'', or R''' groups attached to the same carbon or nitrogen, each R', R'', R''' may be the same as or different from the other R', R'', R''' groups attached to that carbon or nitrogen; admixed with a pharmaceutically-acceptable topical vehicle.

2. The method of claim 1, wherein said retinoid compound comprises from about 0.01% to about 0.5% by weight of said composition.

3. The method of claim 1, wherein said retinoid compound comprises from about 0.05% to about 0.2% by weight of said composition.

4. The method of claim 1, wherein said vehicle is propylene glycol-ethanol and an antioxidant.

5. The method of claim 1, wherein said retinoid compound is 1-(all trans-retinoyloxy)-2-propanone.

* * * * *